(12) United States Patent
Small (10) Patent No.: US 8,942,433 B2
(45) Date of Patent: Jan. 27, 2015

(54) SYSTEM FOR SCHEDULING, RECORDATION AND BIOMETRIC VALIDATION OF INTERPERSONAL INTERACTIONS

(76) Inventor: Luke Small, Kansas City, MO (US)

(*) Notice: Subject to any disclaimer, the term of this patent is extended or adjusted under 35 U.S.C. 154(b) by 1162 days.

(21) Appl. No.: 11/949,766

(22) Filed: Dec. 3, 2007

(65) Prior Publication Data

US 2008/0130957 A1 Jun. 5, 2008

Related U.S. Application Data (60) Provisional application No. 60/868,294, filed on Dec. 1, 2006.

(51) Int. Cl.
| | | |
|---|---|---|
| G06K 9/00 | (2006.01) | |
| G06F 21/32 | (2013.01) | |
| G06F 19/00 | (2011.01) | |
| G06Q 50/10 | (2012.01) | |

(52) U.S. Cl.
CPC .............. *G06F 21/32* (2013.01); *G06F 19/322* (2013.01); *G06Q 50/10* (2013.01)

USPC ........................................... 382/116; 713/156

(58) Field of Classification Search
USPC .................... 382/115; 340/5.83; 1/1
See application file for complete search history.

(56) References Cited

U.S. PATENT DOCUMENTS

| | | | | |
|---|---|---|---|---|
| 7,162,475 | B2 * | 1/2007 | Ackerman ........................... | 1/1 |
| 7,415,456 | B2 * | 8/2008 | Benco et al. ......................... | 1/1 |
| 2001/0026632 | A1 * | 10/2001 | Tamai ............................ | 382/116 |
| 2001/0032310 | A1 * | 10/2001 | Corella ........................... | 713/156 |
| 2002/0158750 | A1 * | 10/2002 | Almalik ......................... | 340/5.83 |
| 2002/0196125 | A1 * | 12/2002 | Yu et al. ......................... | 340/7.48 |
| 2004/0029569 | A1 * | 2/2004 | Khan et al. .................. | 455/414.1 |
| 2004/0082831 | A1 * | 4/2004 | Kobashikawa et al. .......... | 600/38 |
| 2004/0148392 | A1 * | 7/2004 | Cotte ............................. | 709/225 |
| 2004/0152511 | A1 * | 8/2004 | Nicely et al. ..................... | 463/27 |

* cited by examiner

*Primary Examiner* — Hadi Akhavannik
(74) *Attorney, Agent, or Firm* — Bradley IP, LLC; Sean T. Bradley (57) ABSTRACT

A system for scheduling and recording interpersonal interactions using biometric validation to verify user identity and assure user conformance with preselected criteria upon which approval of an interpersonal interaction is contingent.

10 Claims, 10 Drawing Sheets

Fig. 2
User Registration

Fig. 4
Medium Initialization/Registration to a User

Fig. 5A

Meeting Process

Fig. 6

Use of device and server public keys for security.

Fig. 7

SYSTEM FOR SCHEDULING, RECORDATION AND BIOMETRIC VALIDATION OF INTERPERSONAL INTERACTIONS

CROSS REFERENCE TO RELATED APPLICATION

This application claims the benefit of the prior filed, co-pending provisional patent application Ser. No. 60/868,294, filed Dec. 1, 2006, which is hereby incorporated by reference.

BACKGROUND OF THE INVENTION

The present invention relates generally to interpersonal communication systems and more particular to a system for storing and retrieving person information used as selection criteria for interpersonal interactions.

Cellular telephone technology allows users to initiate and maintain communications almost regardless of location. In addition, most cellular telephone handsets (cell phones) provide for transmission of text via email and text messaging as well as conventional voice communications. Further developments include recordation and transmission of digital photographs and video. Therefore, through current cell phone technology, users can communicate a wide variety of types of information to one another. For example, individuals who have never met before can communicate via cell phone and not only gain recognition of one another's voice patterns and qualities but also, through use of integral digital cameras, view one another's facial characteristics. This ability to introduce oneself through both voice and video can prove helpful, for example, to aid recognition at a later in-person meeting.

In order to secure and authenticate use of cell phones and any information that may be recorded and transmitted, some cell phones are provided with software-based security measures such as password protection. Further security may be obtained through use of cell phones having biometric identification devices such as fingerprint scanners. A fingerprint scan records the characteristics of the pad of a person's fingertip including patterns of ridges (epidermal ridges) and furrows that form arches, loops and whorls. A digital image of the fingerprint is processed by software that maps minutiae points as they are located relative to one another. Minutiae point data may be processed by an algorithm to encode the data in a character string that is typically stored within a database and then searched relative to further, subsequent scans of the same fingerprint. Another means of comparing scanned to previously stored fingerprint data includes correlation based matching, which superimposes stored and scanned fingerprint images and calculates the correlation between corresponding stored and scanned pixels. To avoid fraudulent duplication of fingerprint images, a scanned image itself is often not retained by the system or scanner; only the processed data is stored.

Further methods of generating or obtaining unique biometric data include retinal and iris scans. A retinal scan reads the pattern of blood vessels in the back of the eye. An iris scan reads patterns of color variations as well as patterns of striations in the iris. As with fingerprints, such patterns in the retina and iris are unique to each individual.

Although such security measures may be used to authenticate usage of a device or system, what is needed is a method of authenticating interpersonal interactions such that meetings or other interactions with heretofore unknown individuals may be engaged in with a high degree of confidence in personal health and security through positive identification of another both as to identity and as to conformance with preselected criteria or parameters.

BRIEF SUMMARY OF THE INVENTION

A system for assuring secure interpersonal interactions between system users may include a mobile communication device such as cellular telephone, land line telephone, satellite telephone, or other personal communications device, or a stationary communications device such as a kiosk or wall-mounted terminal with telephonic, Internet or equivalent communication capability. Although the embodiments disclosed herein principally contemplate communication through established cellular telephone networks, it should be appreciated that other forms of wireless communication, including any means of communication using transmission and reception of electromagnetic radiation, may be utilized if adapted for conveying information.

The communication device may be provided with means for accepting the input of user biometric identification information, such as fingerprint, iris or retinal scans. Such biometric information may be read by the communication device itself, by an attached scanning device, or by remote devices in electronic communication with the communication device. Biometric data is generated from such information and stored in a data-processing system, typically comprising one or more system computer servers. Biometric data is linked within the system to other identifying or informational data associated with the system user such as name, age, sex, address, communication means identification code, health information and status, and criminal justice system information and status. Under selected parameters, a first user may access the system to confirm the identity of a second user prior to an interpersonal interaction, such as a meeting, and to confirm whether the data associated with the second user conforms to preselected criteria established by the first user.

An objective of certain embodiments of the present invention is to provide a safe system and method for individuals to meet, particularly in situations that would otherwise tend to compromise safety, by recording the identity of all participants in the meeting as well as, optionally, the time and place. Many human interactions require a level of trust on the part of the individuals interacting. Most interactions amount to a mutually pleasant and beneficial experience but a minority may result in an unpleasant experience or even harm to one or more participants. Kidnapping, rape and/or homicide do occur in a small, though important, number of occasions in which an individual agrees to meet with another, previously unknown individual. A system according to the present invention offers means for a first user to positively identify a second user and record, in a secure remote computer system, the time and place of a prospective meeting. The advantages of the system include not only recordation and identification of information that may be of use to a later criminal investigation, should a crime occur, but also prevention and deterrence through positive identification of individuals prior to the meeting.

Another objective of certain embodiments of the present invention is to provide a matching system and method for a user to positively identify and screen other users prior to engaging in sexual activity or other activity known to allow transmission of disease, particularly sexually transmitted diseases. Such embodiments typically include many aspects of the system described above directed to providing safe means for users to meet. Additional elements in a matching system may include health and/or criminal justice information associated with each user record; preselected user criteria for allowing a first user to determine whether a second user presents a significant health or other safety risk; dynamic status indicators that reflect current health status or other factors in response to input by third parties, such as health care providers; and functions for tracking progressive interactions among users and alerting users to potential transmission of disease based on future data received by the system.

In one embodiment, the present invention may comprise a system for assuring secure interpersonal interactions between system users and include a communication means, such as a land-line or cellular telephone, for establishing communications between a system user and a system database, means for acquiring biometric information and providing biometric data derived from the biometric information to the system database, means for comparing the biometric data to a user database record and for providing a system response dependent upon the results of the comparison, acceptance criteria stored in association with a second user database record, means for initiating and transmitting an approval code, dependent upon the acceptance criteria, to the second user, and means for recording in the database the time and place of a prospective meeting between the first user and the second user.

Another embodiment of the present invention may comprise a system for assuring secure interpersonal interactions between system users including an electronic communication means for a first user to communicate with a second user, means for accepting the input of first user biometric identification information, means for generating biometric data from such information and means for storing the information in a data-processing system, means for linking the biometric data within the system to other identifying or informational data associated with the system user, means for a first user to access the system to confirm the identity of a second user prior to an interpersonal interaction, means for confirming whether the data associated with the second user conforms to preselected criteria established by the first user, and means for a first user to record, within the system, the time and place of a prospective meeting with a second user.

Other advantages of the invention will become apparent from the following description taken in connection with the accompanying drawings, wherein is set forth by way of illustration and example an embodiment of the present invention.

DETAILED DESCRIPTION OF THE INVENTION

As required, a detailed embodiment of the present invention is disclosed herein; however, it is to be understood that the disclosed embodiment is merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
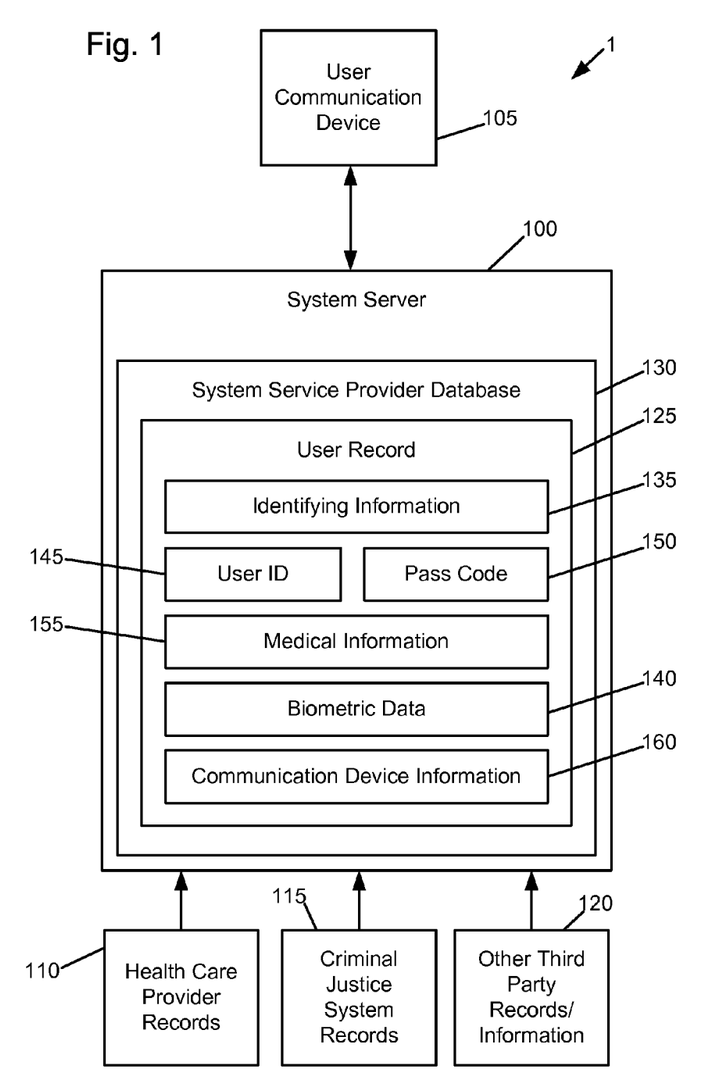
FIG. 1 is a block diagram showing major elements of the system server, a user communication device, and exemplary information sources.
Figure 2:
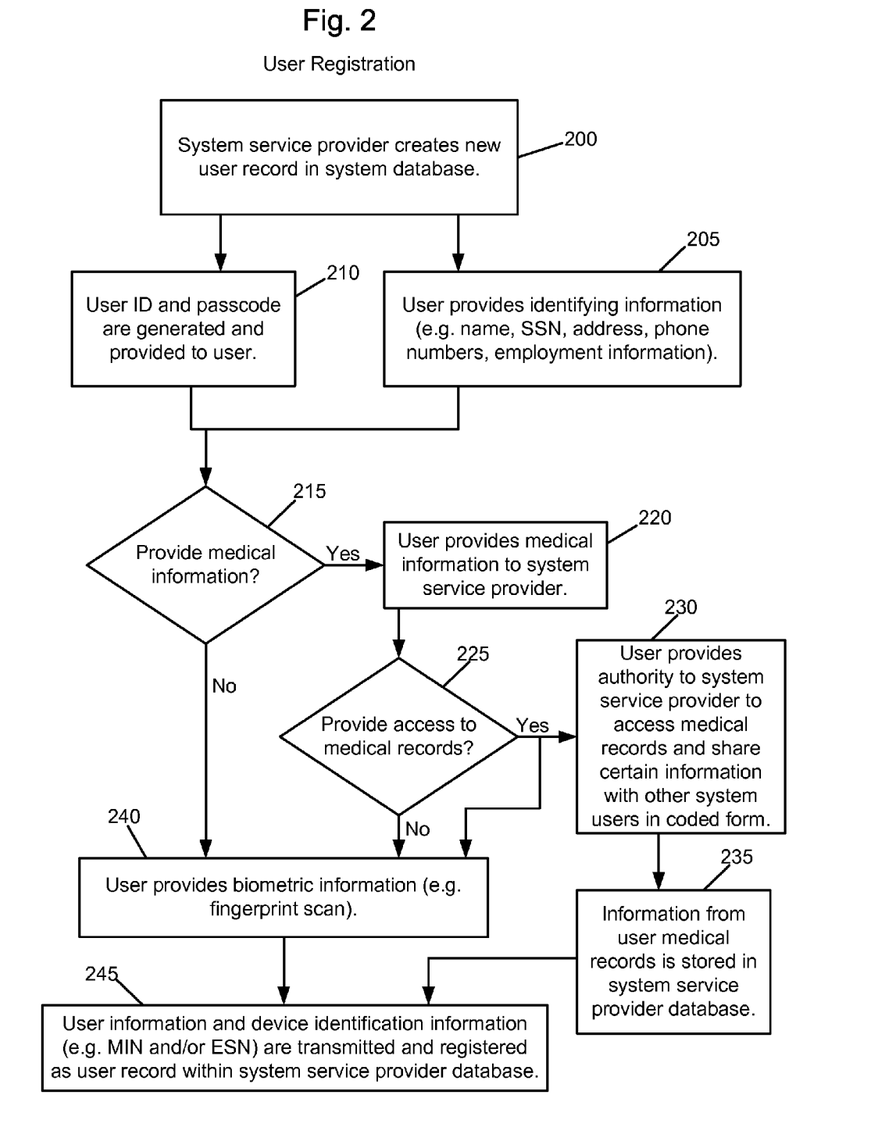
FIG. 2 is a block diagram illustrating a method of registering a user on a system of the present invention.

With reference to the figures, FIG. 1 is a diagram showing major elements of the system server 100, a user communication device 105 for user access to the system, and exemplary information sources such user health care provider records 110, user criminal records 115, and other third party records 120 providing information corresponding to a system user. FIG. 2 illustrates registration of a user on the system 1 of the present invention. The system 1 includes a system server 100 for storing data, including data specific to the user, and for hosting software. Initially, a record or account is opened or created 200 for the user by a system service provider, or by a third party agent or associate of the service provider. This user record 125 is created in a system database 130 resident on the server 100 and accessible by the service provider. The user record 125 is subsequently used to control access to the system 1 and to facilitate system processes. The user provides 205 the service provider with identifying information 135 which may include the user name, social security number, address, phone numbers, employment information, and/or biometric data 140. Either before or after the user provides identifying information 135, a user ID 145 and pass code 150 are generated 210 either by the service provider or by software associated with the system 1 and are provided to the user. Next, a determination 215 is made as to whether the user will provide medical information to be entered into the system. The determination may be made by the service provider and enacted by system software (system software is typically resident on the server or associated computer hardware), or may be a selection offered to the user during registration. If the user will provide information, the user approves or authorizes 225 access to medical records 110 by the service provider so that the system service provider may obtain user medical records from a health care provider such as those maintained by a personal physician, hospital or clinic. Medical information may also be provided by the user to the service provider 220.

User medical information may be associated with the system 1 in any of the following manners. A form may be provided for the user to provide authorization 230 to the system service provider. This form may then be transmitted by regular mail, fax, e-mail or other method to the health care provider. The health care provider may then compile the requested medical information and transmit it by any means to the system service provider where relevant information is entered 235 into a data base record 155 that is associated with the user record 125. Alternatively, a medical professional may receive personal identification information associated with the user like a personal identification number (such as social security number) and name that would prompt opening and access to the user's health record with the health care provider. A sub-routine in the health care provider database can then be invoked which would cause health care data associated with the user to be transmitted electronically directly to the system data base for association with the user record. As a further alternative, access approval generated by the service provider could be transmitted electronically to the health care provider thereby opening a link to the health care provider medical records 110 associated with the user. In this case, health care data would not necessarily be transmitted at this time but access would be granted for the future if a need should arise. As a further alternative, the medical records 110 maintained by the health care provider could be accessed electronically by the system such that data contained in the medical records 110 would cause entry or selection of variables in coded fields maintained by the system 1 such that a secure profile would be created within the system data base 130 without actual transfer of user medical records 110. Typical health care information required by the system may include information related to disease, sexual fertility information, birth control information, sterilization information, immunization information, and check up status information.

Access by the health care provider to the system data base 130 could be timed to prevent access after a certain time period. In addition, access of health care provider information by the system could be timed to avoid security breech by an unauthorized user, with subsequent access to be granted upon further user approval.

User attributes that may comprise the user profile stored within the user record 125, and may be selected as factors in the user's selection profile, include, but are not limited to: age, gender, race, height, weight, body mass index, body fat percentage, hair color, hair type (curly, straight), hair length (short, medium, long, measurement), religion, intelligence quotient, bust measurement, waist measurement, hip measurement, musculature, penis length, bra cup size, education level, income, total assets value, spoken languages, native language, accent (indiscernible, US (north eastern, midwestern, southern, western, hispanic), Canadian, British, Australian, Irish, Scottish, French, Spanish, Italian, German, Indian), drinking habits (never, rare, rare socially, often socially, often, alcoholic, recovering alcoholic), political preference (liberal, moderate, conservative, neo-conservative, libertarian, socialist, communist, fascist), political party (Democrat, Republican, Independent, Libertarian, Green, Communist), habitation (living with: parents, roommate, partner, alone, young children, older children), sexually transmitted diseases (HIV, herpes, hepatitis A, hepatitis B, Chlamydia, gonorrhea, syphilis), fertility/potency status (permanently sterile, taking short term systemic birth control, using prophylactic birth control, taking long term systemic birth control, fertile/potent), criminal status (felon, non-felon), criminal type (armed robbery, robbery, burglary, assault, homicide, sex offender, child sex offender, sexual assault, prostitution, alcohol related, drug related), average visual rating (cumulative average rating by other users), locality (city, state, country), distance (distance from user's location), present locality (GPS coordinates, locality data entered into system), and departure date and time from present locality.

Attributes specifically available in the selection profile to eliminate users from selection may include, but are not limited to: friend (true, false, platonic only), blind date (true, false), sexual interest (true, false), and brief rendezvous (true, false). Advanced options may include ability to enter a text search string.

Information from user medical records 110 is stored 235 in the system service provider data base 130 or is linked to the health care provider data base. Whether revision of medical information 155 is required or not, the system service provider collects 240 user biometric information, for example a fingerprint, iris or a retinal scan. Optionally, the user may provide a blood sample for either immediate typing confirmation or for archiving with a third party service. Biometric information may be collected by the system service provider instruments or may be collected through a communication device 105, such as a cell phone, to be used by the user to interface with the system. The user information and communication device identification information 160, for example MIN and/or ESN, are transmitted and registered 245 within the user record 125 on the system service provider database 130.

Figure 3:
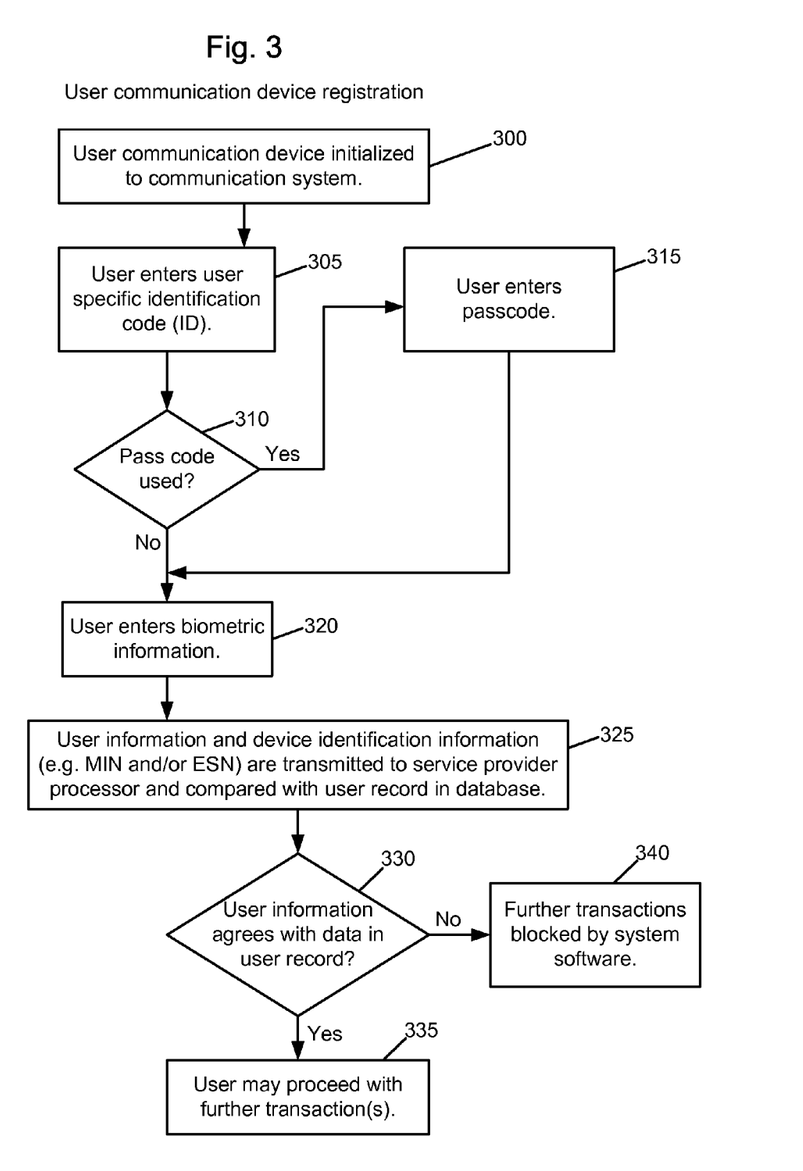
FIG. 3 is a block diagram illustrating a method of registering a user communication device on a system of the present invention.

The user communication device 105 registration is described in FIG. 3. The user communication device 105 is first initialized to the system 1, typically following power up of the device 105. Initialization establishes a communication link to the system, typically a telephonic communication link through a cellular network. Initialization is typically commenced as an automated function of the user communication device and the communication system protocols.

To effect initialization 300, the user enters 305 a specific identification code which identifies the user to the system 1. If a passcode is required 310 the passcode is entered 315 as well. Next the user enters biometric information 320 such as a fingerprint scan. A scan is entered through a scanner provided on the communication device such as a fingerprint scanner provided on a cell phone. User information and device identification (MIN and/or ESN) are transmitted 325 to the service provider processor associated with the system and compared 330 with the user record in the system database. If the user information agrees with correlated data in the user record the user may proceed 335 with further transactions. If the user information does not agree with correlated data of the user record, further transactions are blocked 340 by the systems software.

The above user communication device registration may also be accomplished as follows. First, the user communication device, typically a cell phone, is powered up and allowed to initialize to a communication system such as a cell phone network. The system database is queried using an ID and passcode entered into the communication device by the user. A user record or account is opened or accessed in the system database. Biometric data entered by the user, typically through a finger scan, is stored at least temporally in a user identified record. Software on the communication device may offer the opportunity to the user for multiple scans to be taken, either for averaging purposes or for rejection of outliers. One or more of the scans or an average composite of a scans are then compared for agreement with specified parameters stored in the data base and associated with a prior biometric scan taken at user initiation to the system.

Figure 4:
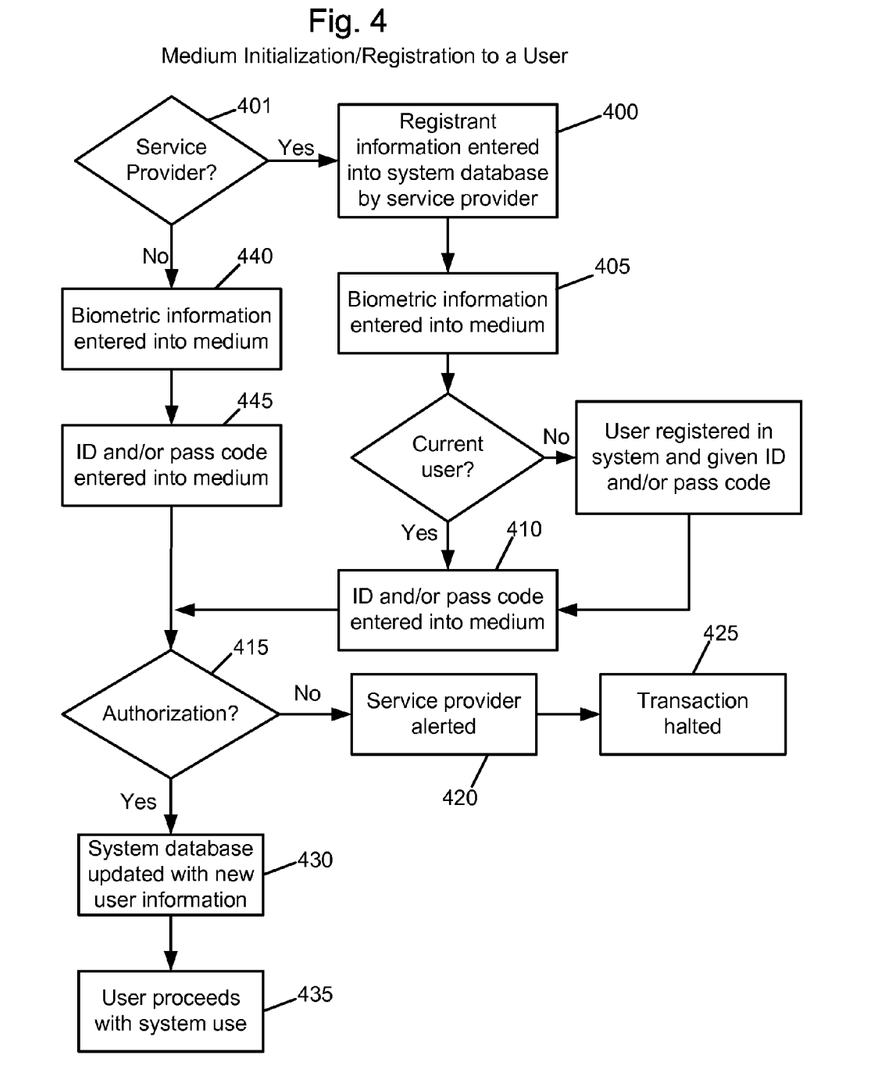
FIG. 4 is a block diagram illustrating a method of initializing a communication medium to a user.

FIG. 4 discloses and describes medium initialization or registration to a user. Initial registration of a communication device or a medium to a user may be performed by a system service provider 401, preferably at the service provider business location. Initial registration of the medium and user is followed on subsequent uses by user initialization.

Registrant name, address, social security number and other identifying information are taken and entered 400 into the system by the system service provider. Using either the communication device or medium or secure service provider instruments, biometric information is entered 405 by a fingerprint scan and/or retinal scan as further identification confirmation. If the user has been previously registered on the system the user ID code and/or passcode are entered 410. All information entered into the system is processed by the system to check for accuracy, conflicts, and to establish the identity of the user and to check for authorization 415 to use the system. For example, the system will check to see if the user has been blocked from access or otherwise targeted due to a problem or incident such as criminal warrant for arrest, onset of a targeted disease, failure to pay system fees, etc. If authorization fails, the service provider is alerted 420, the transaction is faulted and service is frozen 425. If the user is authorized by the system the database may be updated 430 with new information if any and the user may proceed 435 with further use of the system. If a service provider is not used, the user enters 440 biometric information into the user's communication device, followed by the user's passcode and/or ID 445.

To uniquely identify a communication device or medium from an unauthorized medium, such as one in which all stored data has been copied from the original medium perhaps after a theft of the original medium. A code may be used which is constantly refreshed by the medium and transmitted to the system server, preferably with every new medium-to-server transaction. Another code may be generated by the server and transmitted to the medium to verify the authenticity of the server. The server code may be generated in conjunction with a renew date and set of server information. (See FIG. 7) A user entered ID or passcode may not be necessary as the user may be identified by the system solely on the basis of the scanned biometric information. The use of an ID and/or passcode, however, provides a much less processing-intensive means for the server and/or database software to quickly identify the user record. In addition, passcodes can serve as security function by restricting system access based solely on biometric information which can otherwise be entered by surreptitious or course if needs such as passing the finger of a sleeping or unconscious person or forcing a person to scan their finger under duress. In addition, passcode protection will allow a user to enter a distress code when under coercion thereby alerting the system to an emergency. In such a case, automated system functions can then be initiated to contact emergency personnel, both governmental and private, and to invoke system emergency locations such as medium location via cell phone, tower triangulation or GPS.

Entry of a distress code could additionally cause the system to freeze system account activity or to feign ignorance of an account. Additionally, medium specific emergency routines could be invoked such as recordation and/or transmission of audio and/or video generated by the medium within range of the mediums microphone and/or camera.

Optionally, the duration and location of the meeting may also be recorded, particularly if cell phone tracking is enabled in which case location data may be generated and stored at time intervals or at points at which the tracking system notes significant movement of a parties' cell phone. A meeting location should be selected with personal security in mind. Ideally, a meeting would occur at a location where all participants are secure in the ability to opt out at any time at least during registration of the meeting. A party must have the ability to decline a request for a meeting and walk away. As a rule of meeting protocol, all participants provide identification including identifying means such as user ID, passcode, and biometric information generated from a contemporaneous stand.

Figure 5A:
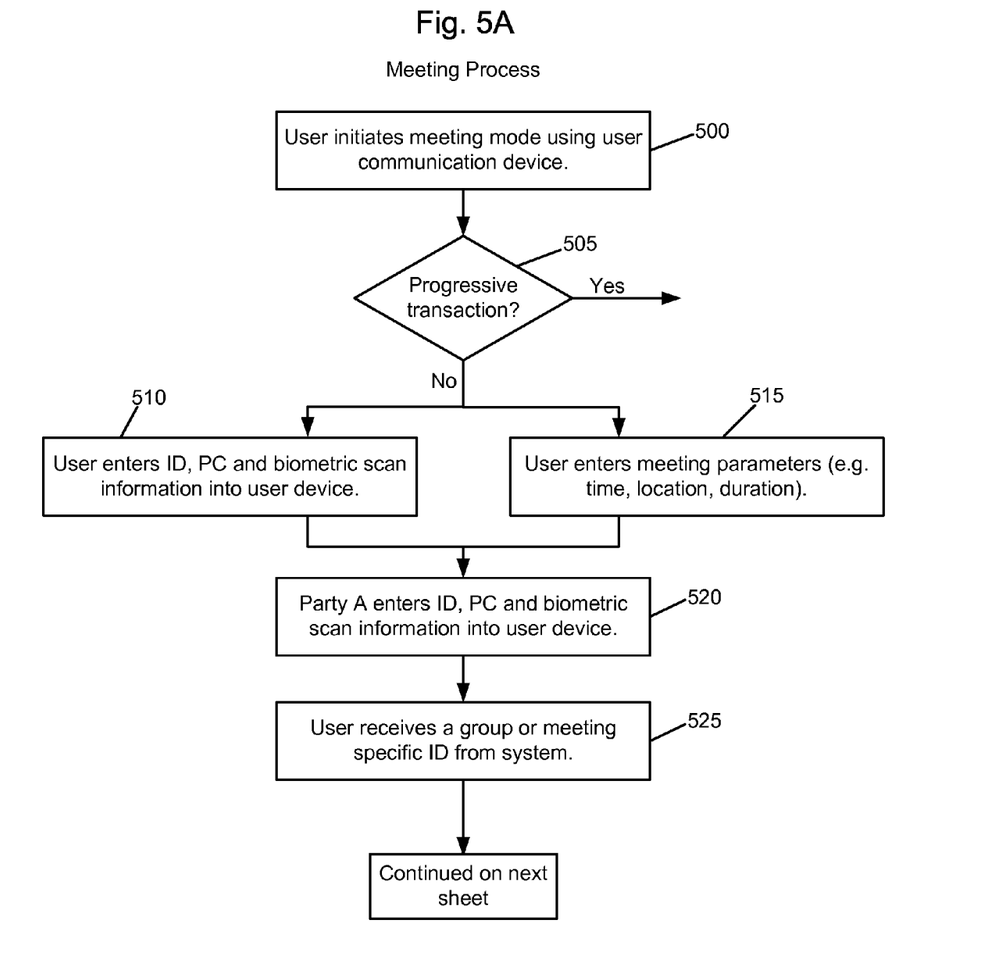
FIG. 5A is a block diagram illustrating a method of initiating a meeting facilitated by a system of the present invention.
Figure 5B:
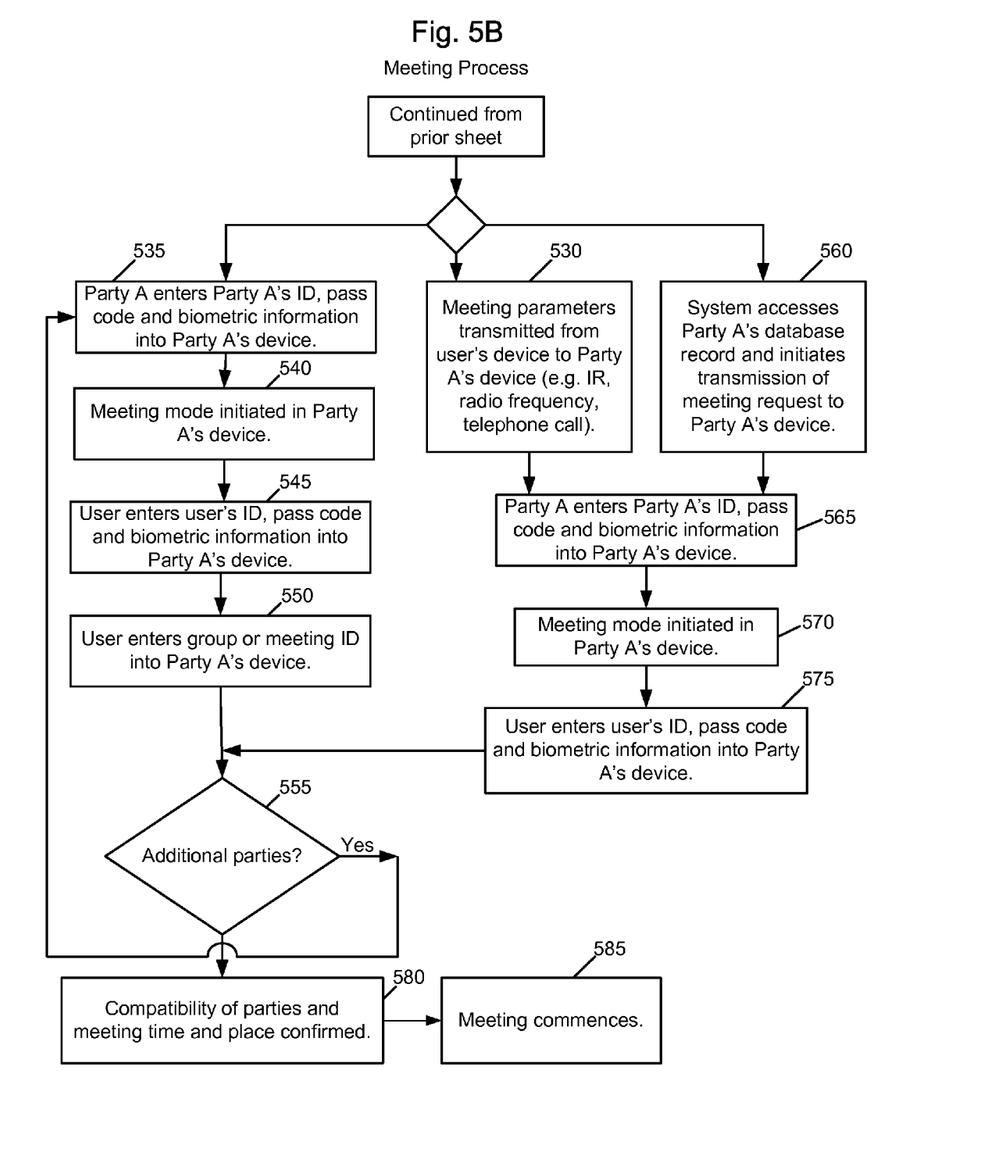
FIG. 5B is a continuation of the block diagram of FIG. 5A.

FIGS. 5A and 5B describe processes associated with setting up and/or initiating a system controlled and monitored meeting process. Initially, a user initiates 500 a system meeting mode using the user communication device or medium. Next a determination 505 is made as to whether this will be a progressive transaction. The user enters 510 an ID and/or passcode and a biometric scan into the medium. The user then enters 515 meeting parameters, for example time, location and duration. The user will then indicate through a selection entered into the medium that he or she is done entering meeting parameters. A meeting may be set up to include several parties in addition to the user. Optimally, all parties to the meeting will be account holders on the system so that the entry of identification codes and/or passcodes and biometric information identity may be established and confirmed through the system software. However, the system will still be utilized to record meetings with persons not registered on the system through entry of party names using keypad buttons on the medium and, more particularly, by scanning party biometric information which can then be transmitted by the medium for storage by the system.

After the user has entered personal information and registered on the system, Party A enters Party's ID and/or passcode 520 and completes a biometric scan on the user device. It is important that Party A enter all information including the scan on the user device because the user would likely know whether his or her device has been tampered with. If Party A is allowed to enter identification data and biometric scans in his or her own device the user would have no guarantee that such data could not be altered or supplanted by either software resident on Party A's medium or by intermediary software accessed by Party A's medium prior to transmission to the system. Either prior to or subsequent to entry of Party A information into users device, the user may receive 525 a group or meeting specific identification code from the system. A meeting specific ID is generated in one of the following ways:

A. The system generates the meeting ID randomly and the system checks to assure that the meeting ID does not conflict with any prior issued ID:

B. The system maintains a finite listing of meeting IDs which are issued on a temporary basis, thus assuring no meeting ID is in use more than once at the same time. This meeting ID is used during accesses associated with the particular meeting until the meeting no longer exists or the meeting ID usage period expires. The finite number of meeting IDs may also serve to limit system network traffic; or D. A user ID or other non-temporary ID such as a group ID is also used as a meeting ID.

After the user receives the group or meeting specific ID 525, meeting information may be transmitted 530 to Party A's device at this time by a radio signal, infrared signal or by initiating the call to Party A's device through the telephone system. Alternatively, the user could enter a group or meeting ID code provided by the server and enter it along with user biometric information into Party A's device. Party A's device will then send such information to the server and receive back meeting information to be provided to Party A through the device. Additionally Party A's device could thereby be prompted by the system for further needed action.

At least three different means of transmitting information to Party A's device may be used. Party A may initiate transmission of meeting parameters to Party A's device by first registering on the system. For example Party A enters Party A's ID and/or passcode and biometric information into Party A's device to register on the system 535. A meeting mode is then initiated 540 by Party A and Party A's device. Party A enters their ID and/or passcode and biometric information into Party A's device 545 and also enters the group or meeting identification code provided by the system into Party A's device 550. If additional parties are to be added 555 to the meeting the above steps may be repeated for Parties B, C, D, etc.

Alternatively, prior to registration of Party A's device, meeting parameters may be transmitted 530 from the user's device to Party A's device through a call to the telephone system, radio transmission, or transmission through IR (infrared) communication ports. Codes associated with such transmission will invoke a meeting mode in Party A's device or will be stored for access after Party A's system registration. Alternatively, rather than direct transmission from the users device to Party A's device, the system itself may access Party A's database information/record and initiate transmission 560 of a meeting request to Party A's device.

If either the user or the system initiates transmission to Party A's device a meeting request signal or icon may be displayed upon Party A's device alerting him or her to the meeting request. Party A will then enter 565 Party A's ID or passcode and biometric information to register Party A's device upon the system and the meeting mode may be initiated 570 by Party A in Party A's device. However initiation of meeting mode or transmission of meeting request information to Party A's device occurs, both Party A and the user should enter 575 their respective IDs and/or passcodes and biometric information into each others devices as a way of securely confirming the other party's identity. Once all parties have responded to the meeting request initiated by the user, the compatibility of the parties and of the meeting time and place specified by the user are confirmed 580. At this point the meeting may commence 585. By each party entering his or her own identification and/or passcode and biometric scan into their own device, typically in response to a meeting request communicated by a user device or by the system, confirmation of each party's identity and acceptance of the meeting requests as well as assurance of each party's agreement and security at the time of confirmation is assured.

An example of a further embodiment of a progressive transaction according to the present invention is as follows. Party X meets previously unknown Parties Y and Z. Parties X, Y and Z decide to meet at another location and the system of the invention is used to assure mutual security and safety. Party X allows Party Y to enter Party Y's identifying information into Party X's medium. Confirmation of Party Y's identity (and any warnings or flagged information generated from system comparison of Party X's profile to Party Y's profile) is received by Party X on Party X's medium. The system prompts Party X to indicate whether the transaction is to be progressive. Party X makes the proper entry or selection, typically on a medium keypad or via voice, to indicate in the affirmative. Party Y allows Party X to enter Party X's identifying information into Party Y's medium. Confirmation of Party X's identity (and any warnings or flagged information generated from system comparison of Party Y's profile to Party X's profile) is received by Party Y on Party Y's medium. Party X allows Party Z to enter Party Z's identifying information into Party X's medium. Confirmation of Party Z's identity (and any warnings or flagged information generated from system comparison of Party X's profile to Party Z's profile) is received by Party X on Party X's medium. Party Z allows Party X to enter Party X's identifying information into Party Z's medium. Confirmation of Party X's identity (and any warnings or flagged information generated from system comparison of Party Z's profile to Party X's profile) is received by Party Z on Party Z's medium. It should be appreciated that the above routine may be repeated ad infinitum within the constraints of the system.

If an alert or alarm should be generated by the system after the meeting takes place, all members of the progressive transaction are notified even though not every member registered individually with every other member. All members of the transaction may register through the member initiating the progressive transaction, the primary member (Party X above), or, in less controlled progressive transactions, may register through secondary members such as Party Y or Z.

A potential member of a progressive transaction may have pre-specified criteria associated with their account that limits the types of progressive transactions to which they may remain party. For example, Party Z could have it specified that he or she will only allow their participation in progressive transactions wherein all members register through the primary member. If Party X specifies or selects a progressive transaction that is not thus limited, Party Z will therefore receive an alert upon attempting registration to the transaction. Alternatively, if Party X does not specify limitations to the transaction, but later a secondary member registers a tertiary member, Party Z will be alerted by the system.

Figure 6:
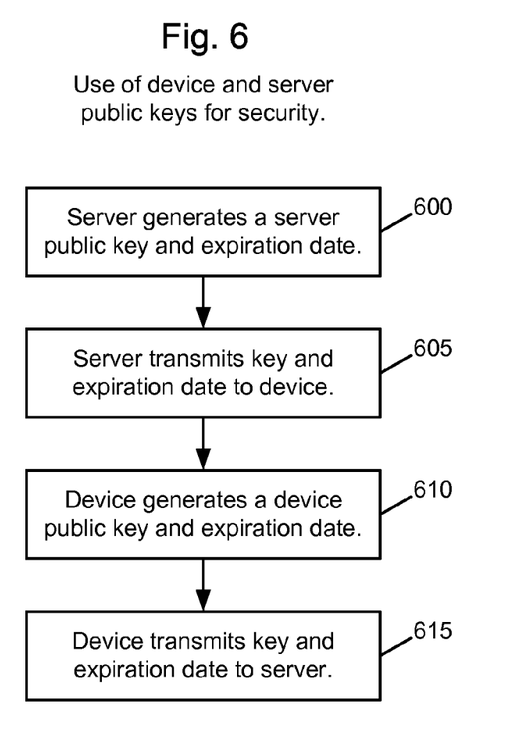
FIG. 6 is a block diagram illustrating initial setup of public keys for identification and authentication of a system server.
Figure 7:
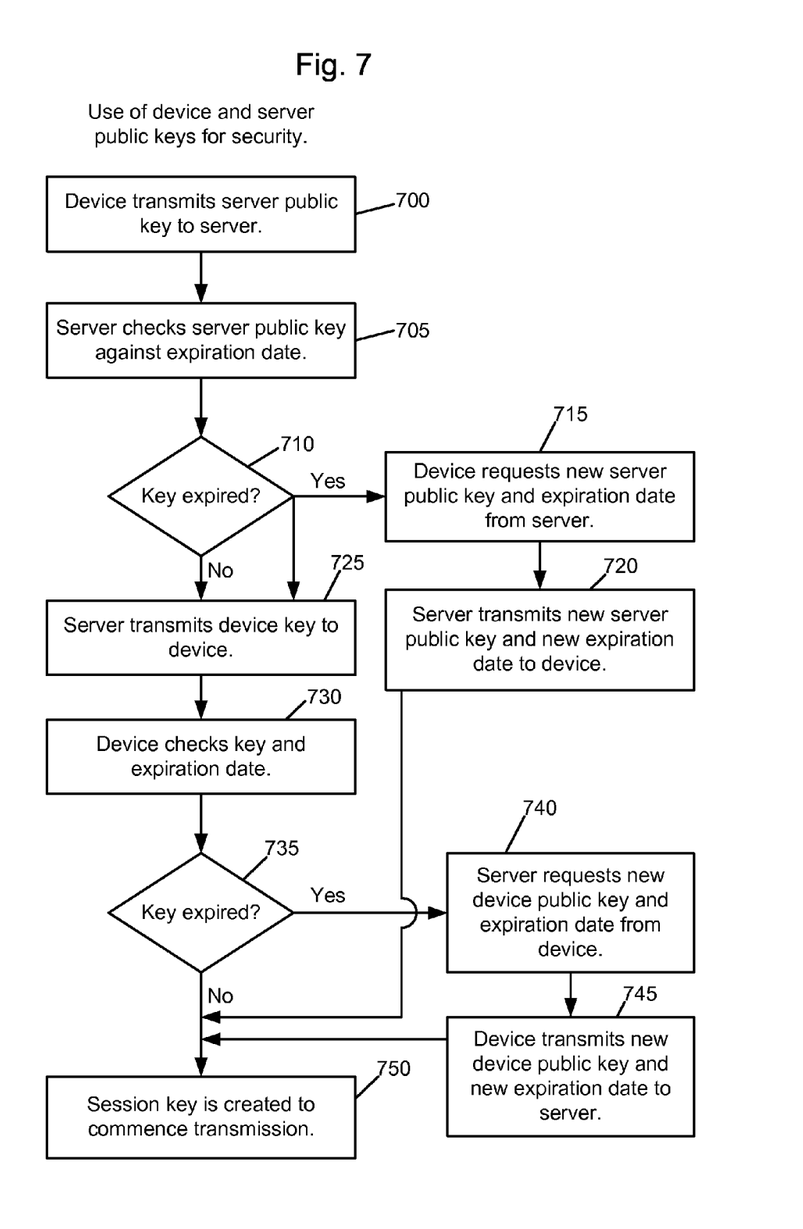
FIG. 7 is a block diagram illustrating initial setup of public keys for identification and authentication of a system server.

FIG. 6 describes the use of the communications device or medium and server public keys for security. First, the system server generates 600 a server public key and expiration date for that key. The server transmits 605 the key and expiration date to the user device. The device generates 610 a device public key and expiration date and transmits 615 the key and expiration date to the server. This routine constitutes initial key setup. FIG. 7 discloses use of the keys for secure transmissions following initial setup.

To securely register a device on the system the following steps may be followed as disclosed in FIG. 7. The device transmits 700 the stored server public key to the server. The server checks 705 the server public key against the expiration date. If the key is expired 710, the device requests 715 a new server public key and expiration date from the server. The server transmits 720 a new server public key and new expiration date to the device. The server also transmits 725 the device key to the device and the device checks 730 the key and expiration date. If the device key has expired 735, the server requests 740 a new device public key and expiration date from the device. The device transmits 745 a new device public key and new expiration date to the server. Once both the server and the device have non-expired keys generated by each other, a session key is created 750 to commence transmission.

Figure 8:
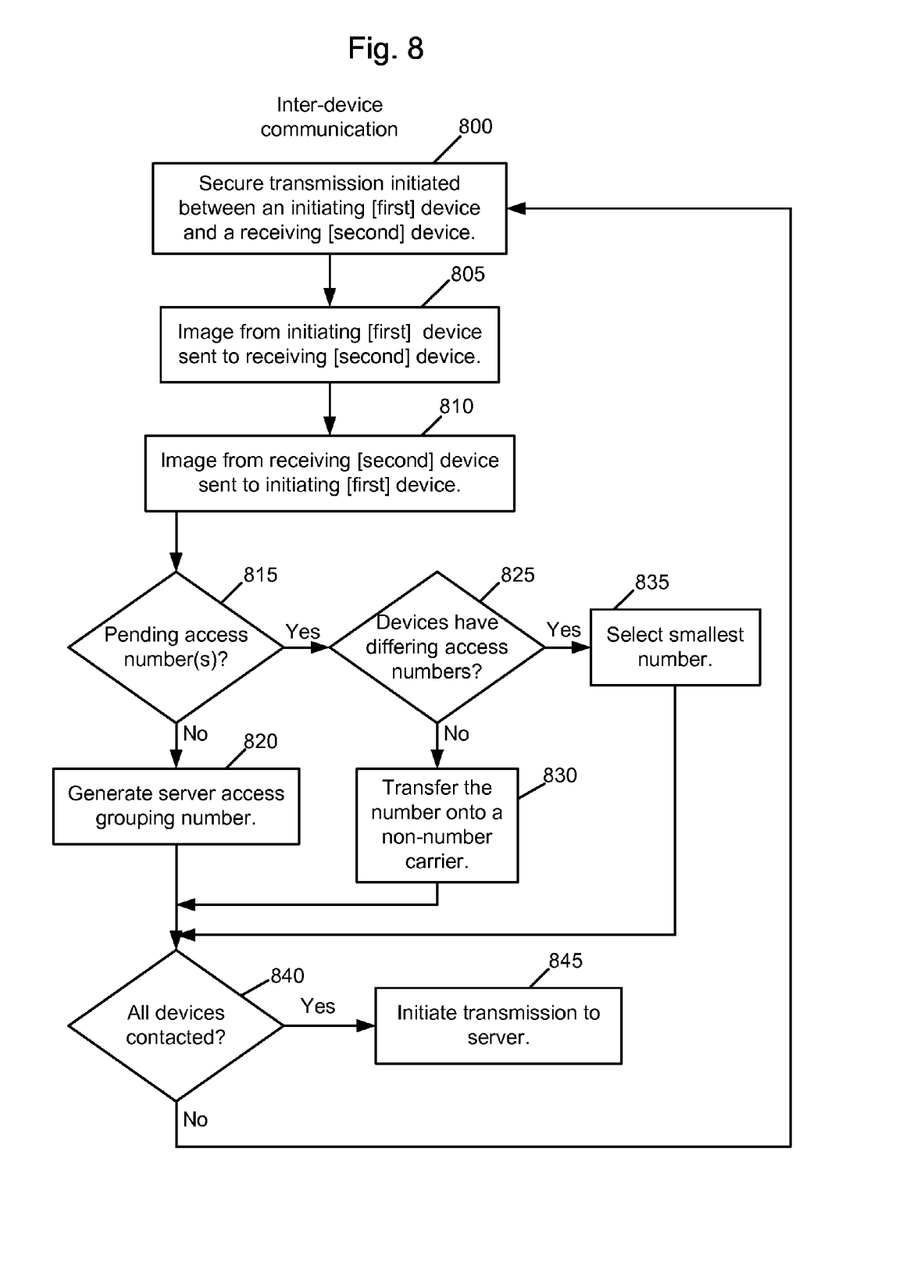
FIG. 8 is a block diagram illustrating a method of inter-device communication.

FIG. 8 describes secure transmissions between devices associated with the system. A secure transmission is initiated 800 between a first device and a second device. A first user image stored in a first server record corresponding to the first device is sent 805 to the second device. A second user image stored in a second server record corresponding to the second device is sent 810 to the first device. The images are typically digital photographs of users associated with each device and are provided so that each user may be assured of the identity of the other user. It is important, therefore, that the user images by of a quality and kind sufficient for use as identification means. Images such as driver's license and passport photographs are examples of typically appropriate identification images.

A secure transmission may be made via IR communication transfer between first and second devices, or a combination of initial direct IR communication between the devices followed by transmission of further data from the system to the devices.

A check is made by the initiating device as to whether either device has a record of a pending server access number 815. If not, a server access grouping number, such as that associated with a meeting, is generated 820. If there are pending access numbers, and the devices have the same number 825, the number is transferred to a non-number carrier 830. If the devices each have access numbers, but differing access numbers, the smallest number is selected 835 and used as the server access grouping number. A check is then made as to whether all devices associated with the group have been contacted 840. If so, transmission to the server is initiated

845. The server receives a medium access request transmitted by an initiating device. The server checks to determine whether the meeting requires more accesses to fulfill the meeting parameters. If so, the system remains open for another medium access to the same specified group within a particular time limit. If the time limit expires, the group or meeting will fail. (See FIG. 8.)

In a further embodiment of the present invention, referred to herein as "call allow", a telephone call placed by a first party over an existing telephonic communication system to a second party is only allowed to connect with the second party if the second party has previously initiated an allow function, either through the second party's account or through a selection or entry made locally in the second party's communication device or medium such as a cell phone. For example, an allow function may be initiated by approval of the first party's telephone number within the second party's account or cell phone. Thereafter, telephone calls emanating from the first party's cell phone (or other telephones associated with the first party's account) will be allowed to connect to the second party's cell phone. The call allow function is particularly useful in situations wherein the second party's telephone number becomes publicly known (or otherwise more widely available than desired by the second party), because calls from non-approved callers (i.e. calls from cell or land line phones whose telephone numbers have not been selected for approval by the second party) will be blocked by the system. Land-line telephones or other communications devices may similarly be used to implement call-allow functionality. Further, call forwarding, as known in the prior art, may be integrated so that only allowed callers are forwarded to the secondary telephone number. Optionally, the system may allow first party to use a non-system telephone to call a second party by the first party entering a user identifier (such as the first party's telephone number) and a password into the non-system telephone. After recognition by the system, the first user enters either the telephone number of the second party, if known, or a system generated code previously provided by the second user to the first user to maintain anonymity of the second user's actual telephone number. Such functionality would typically be optional and at the discretion of the second party.

A further implementation would provide for a trusted, allowed caller (Caller A) to be granted rights by the allowing, receiving party (Receiver A) to temporarily register a third party caller (Caller B) on Receiver A's call allow list.

Figure 9:
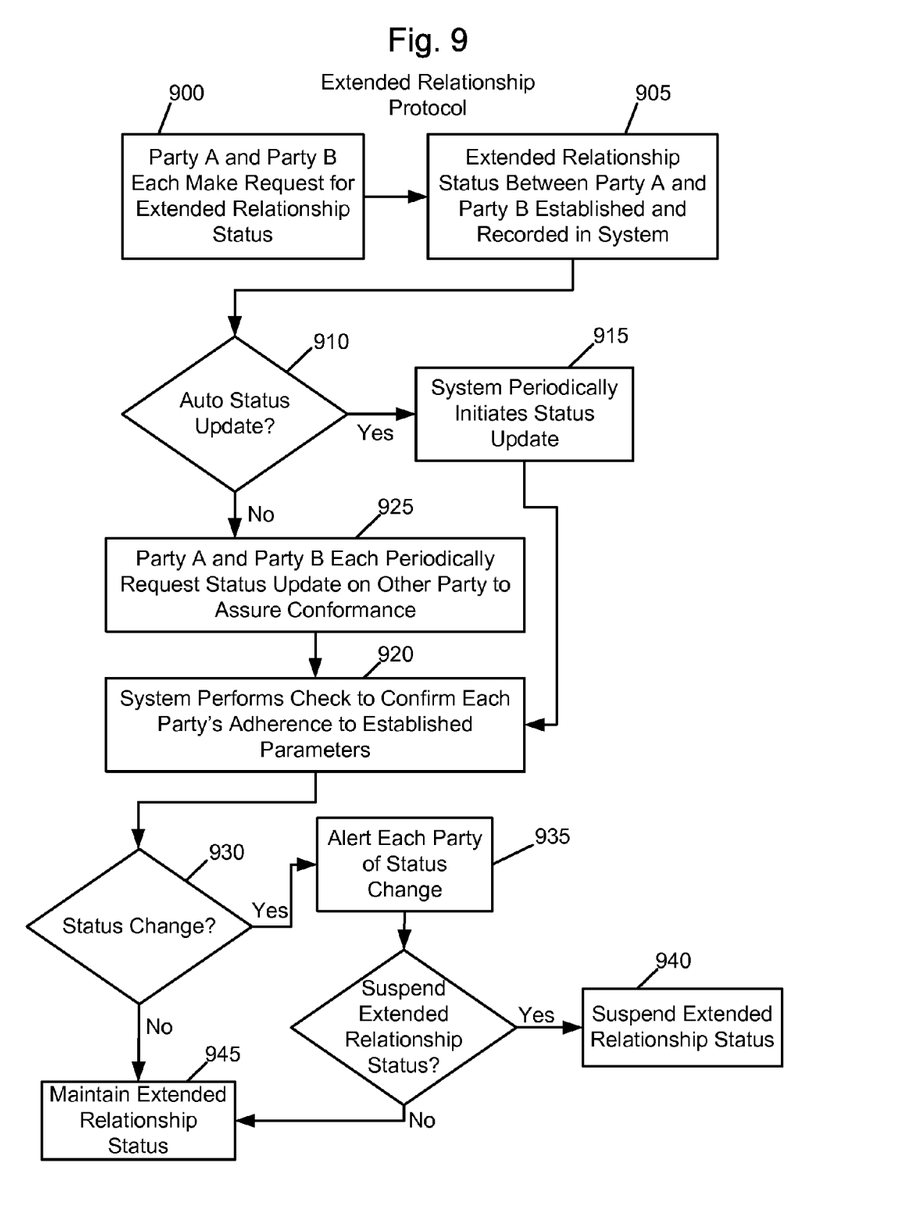
FIG. 9 is a block diagram illustrating a method of initiating an extended relationship protocol.

FIG. 9 illustrates an extended relationship protocol that parties may invoke when an extended relationship, taking advantage of the procedures and protocols of the system, is desired. After registration on the system, parties, for example, Party A and Party B, who desire to invoke an extended relationship protocol within the system, make a request 900 to the system for extended relationship status between the two parties. Typically, this is accomplished by each party making a menu selection, or inputting a code, signifying extended status selection with the system software 905. Each party also enters information (such as telephone number) sufficient to indicate the identity of the other selected extended status party to the system. An Auto Status Update function may be selected 910. If selected, the system periodically initiates a status update 915 wherein the system performs a check 920 to confirm that each party's information adheres to established parameters: either system parameters or criteria/parameters specified by the other party. If auto status update is not selected, the parties are left to periodically request a status update on the other party's information to ascertain conformance to established parameters 925.

Upon completion of a status update or query, the system determines whether a status change has occurred 930. If so, each party to the extended relationship is alerted to the status change 935. The alert may relay specific information, such as a newly arisen health condition or change to criminal record, or, in other embodiments, may simply relay an indication of the existence of a status change to a category of user information, e.g. "Status Change: Health Record." Typically, alerts are conveyed to user communication devices (e.g. cell phones). If the status change causes a party's status to exceed the other party's criteria tolerances, the extended status relationship is suspended or terminated 940. If the status update indicates no change in status, or an acceptable change in status, the extended relationship is maintained 945.

It is to be understood that while certain forms of this invention have been illustrated and described, it is not limited thereto except insofar as such limitations are included in the following claims and allowable equivalents thereof.

Having thus described the invention, what is claimed as new and desired to be secured by Letters Patent is as follows:

1. A system for assuring secure in-person interpersonal interactions, contingent upon data received from secure communications, between system users, the system comprising:
   two or more communication devices for use by system users, said devices comprising means for transmitting and receiving sound and images and means for reading and storing user biometric information;
   a system database for inputting, storing, and outputting information from said communication devices, said database including an individual user record corresponding to each system user, said record including user identification information,
   a user communication device initialized, using a user specific identification code, a user specific passcode and user biometric information, to a communication system for a first user to access the system to confirm the identity of a second user during an in-person interpersonal interaction, and
   means for determining whether data associated with said second user conforms to preselected criteria established by said first user.

2. The system of claim 1, wherein said identification information includes user name, age, gender, biometric data, and communication device identification.

3. The system of claim 1, further comprising means for recording the time and place for a prospective meeting between said first user and said second user in said system database.

4. The system of claim 3, further comprising means for storing identification information corresponding to said first user and said second user.

5. A system for assuring secure in-person interpersonal interactions, contingent upon data received from secure communications, between system users, the system comprising:
   a progressive transaction including:
   a first communication device for establishing communications between a first system user and a system database,
   means for acquiring biometric information from a second system user and providing biometric data derived from said biometric information to said system database,
   first acceptance criteria stored in association with a first user database record,
   means for comparing said biometric data to a second user database record to confirm identification of said second user, and for providing a system response to said communication device dependent upon the results of said comparison, means for initiating and transmitting an approval code, dependent upon said first acceptance criteria, to said first communication device, second acceptance criteria stored in association with a second user database record, means for initiating and transmitting an approval code, dependent upon said second acceptance criteria, to a second user communication device, means for recording in the database the time and place of a prospective meeting between said first user and said second user, and means for initiating a meeting mode using one of said communication devices, means for acquiring biometric information from a third system user and providing biometric data derived from said biometric information to said system database, means for comparing said biometric data to a third user database record to confirm identification of said third user, and for providing a system response to said first communication device dependent upon the results of said comparison, means for initiating and transmitting an approval code, dependent upon said first acceptance criteria, to said first communication device, third acceptance criteria stored in association with a third user database record, and means for initiating and transmitting an approval code, dependent upon said third acceptance criteria, to a third user communication device.

6. The system of claim 5, wherein said biometric data comprises data derived from a fingerprint scan.

7. The system of claim 5, wherein said biometric data comprises data derived from an eye scan.

8. A system for enabling secure interpersonal interactions between system users, comprising:
two or more user communication devices for use by system users, said devices comprising means for transmitting and receiving sound and images and means for reading and storing user biometric information, said devices each initialized to a communication system using a server public key generated by a system server and a corresponding server public key expiration date, said server public key and server public key expiration date transmitted to said devices, said devices generating a device public key and a corresponding device public key expiration date transmitted to said server;

a system database for inputting, storing, and outputting information from said communication devices, said database including an individual user record corresponding to each system user, said record including user identification information, and user information descriptive of the state of said user's health, criminal record and one or more criteria for matching other system users; and means for alerting a first system user if a second system user's information does not meet, or no longer meets, said first system user's criteria.

9. The system of claim 8, wherein said criteria are selected from the group consisting of age, gender, race, height, weight, body mass index, body fat percentage, hair color, hair type, hair length, religion, intelligence quotient, bust measurement, waist measurement, hip measurement, musculature, penis length, bra cup size, education level, income, total assets value, spoken languages, native language, accent, drinking habits, political preference, political party, habitation, sexually transmitted diseases, fertility/potency status, criminal status, criminal type, average visual rating, locality, distance, present locality, and departure date and time from present locality.

10. A method for providing secure interpersonal interactions comprising the steps of:
initiating a meeting mode using a first user communication device, transmitting a first user identification number associated with said first user communication device to a service provider, receiving first user biometric information in said first user communication device, receiving second user biometric information in said first user communication device, transmitting first user and second user biometric information from said first user communication device to said service provider, transmitting a second user identification number associated with said second user communication device to said service provider, receiving first user biometric information in a second user communication device, receiving second user biometric information in said second user communication device, transmitting first user and second user biometric information from said second user communication device to said service provider, receiving confirmation of meeting request from said service provider to said communication devices, and receiving disease information derived from system records and corresponding to both parties to said communication devices.

\* \* \* \* \*